United States Patent
Nakano et al.

(10) Patent No.: US 6,946,578 B2
(45) Date of Patent: Sep. 20, 2005

(54) PROCESS FOR PRODUCING PHENOXYPHOSPHAZENE COMPOUND, FLAME-RETARDANT RESIN COMPOSITION, AND FLAME-RETARDANT RESIN MOLDING

(75) Inventors: Shinji Nakano, Tokushima (JP); Yuji Tada, Tokushima (JP); Tadao Yabuhara, Tokushima (JP); Takashi Kameshima, Tokushima (JP); Yoichi Nishioka, Tokushima (JP); Hiroyuki Takase, Tokushima (JP)

(73) Assignee: Otsuka Chemical Co., Ltd., Osaka (JP)

( * ) Notice: Subject to any disclaimer, the term of this patent is extended or adjusted under 35 U.S.C. 154(b) by 44 days.

(21) Appl. No.: 10/745,255

(22) Filed: Dec. 23, 2003

(65) Prior Publication Data

US 2004/0127734 A1 Jul. 1, 2004

Related U.S. Application Data

(62) Division of application No. 10/030,439, filed as application No. PCT/JP01/03616 on Apr. 26, 2001, now abandoned.

(51) Int. Cl.[7] .............................. C07F 9/02; C09K 21/12
(52) U.S. Cl. ................................. 568/8; 568/9; 568/12; 252/609; 4/6; 4/8; 4/10; 4/12
(58) Field of Search .......................... 568/9, 12; 252/4, 252/6, 8, 10, 12, 609

(56) References Cited

U.S. PATENT DOCUMENTS

| 2,109,491 A | 3/1938 | Lipkin |
| 3,206,494 A | 9/1965 | Lund et al. |
| 3,996,312 A | 12/1976 | Kolich et al. |
| 4,108,805 A | * 8/1978 | Dieck et al. ................ 521/180 |
| 4,440,921 A | 4/1984 | Allcock et al. |
| 4,551,317 A | 11/1985 | Li |

* cited by examiner

*Primary Examiner*—Johann Richter
*Assistant Examiner*—Lansana Nyalley
(74) *Attorney, Agent, or Firm*—Knobbe, Martens, Olson & Bear LLP

(57) ABSTRACT

An improved phenoxyphosphazene compound is produced by treating a phenoxyphosphazene compound with (a) at least one adsorbent selected from activated carbon, silica gel, activated alumina, activated clay, synthetic zeolite and macromolecular adsorbents, (b) at least one reagent selected from metal hydrides, hydrazine, hypochlorites, thiosulfates, dialkyl sulfuric acids, ortho esters, diazoalkanes, lactones, alkanesultones, epoxy compounds and hydrogen peroxide, or (c) both the adsorbent and reagent, thereby reducing the acid value of said phosphazene compound to lower than 0.025 mgKOH/g.

8 Claims, No Drawings

PROCESS FOR PRODUCING PHENOXYPHOSPHAZENE COMPOUND, FLAME-RETARDANT RESIN COMPOSITION, AND FLAME-RETARDANT RESIN MOLDING

This application is a divisional application of U.S. patent application Ser. No. 10/030,439, filed Jan. 2, 2002, now abandoned which is the U.S. National Phase under 35 U.S.C. §371 of International Application No. PCT/JP01/03616, filed Apr. 26, 2001, which was published in a language other than English, which claims priority to Japanese Patent Application No. 2000-132114, filed May 1, 2000. The disclosure of the above prior application is herein incorporated by reference in its entirety.

BACKGROUND OF THE INVENTION

1. Field of the Invention

The present invention relates to a process for the preparation of phenoxyphosphazene compounds, flame-retardant resin compositions and flame-retardant resin molded articles.

2. Description of the Related Art

Phenoxyphosphazene compounds are the oligomers or polymers which are prepared by reacting a dichlorophosphazene compound with an alkali metal salt of a phenol compound. The use of these compounds as additives, modifiers, etc., for synthetic resins has been heretofore studied.

Phenoxyphosphazene compounds can impart high flame retardancy, thermal stability, molding processability and other properties to synthetic resins. However, phenoxyphosphazene compounds have a serious drawback: they discolor synthetic resins when added thereto.

In addition, the addition of a phenoxyphosphazene compound to a synthetic resin may deteriorate the heat resistance, weathering resistance, discoloration resistance, chemical resistance and other properties of the synthetic resin in long-term storage, although such deterioration may not be evident shortly after the addition. Especially, resin compositions prepared by adding a phenoxyphosphazene compound to a polycarbonate resin or a mixed resin of a polycarbonate resin and another resin undergo a decrease in molecular weight of the polycarbonate resins during long-term storage. Inevitably, this results in greatly lowered transparency, change in hue such as whiteness, etc., of the polycarbonate resins.

Phenoxyphosphazene compounds are usually washed with an aqueous solution containing an acid such as hydrochloric acid, sulfuric acid or the like, an aqueous solution containing an alkali such as sodium hydroxide, sodium carbonate or the like or water. However, such washing treatment cannot satisfactorily mitigate the above-mentioned drawbacks of phenoxyphosphazene compounds.

Further, when a molding is produced from the resin composition prepared by adding the phenoxyphosphazene compound washed with the aqueous acid solution or aqueous alkaline solution to a synthetic resin, it corrodes the molding device.

SUMMARY OF THE INVENTION

An object of the present invention is to provide a phenoxyphosphazene compound which prevents discoloration of a synthetic resin when added thereto.

Another object of the present invention is to provide a phenoxyphosphazene compound which can be added to a synthetic resin without deteriorating the properties of the synthetic resin such as heat resistance, weathering resistance, discoloration resistance, chemical resistance and the like even when stored for a long time.

Another object of the present invention is to provide a phenoxyphosphazene compound which can be added to a polycarbonate resin or a mixture of a polycarbonate resin and another resin without substantially reducing the molecular weight, the transparency, hue such as whiteness, etc. of the polycarbonate resin.

Another object of the present invention is to provide a phenoxyphosphazene compound which does not corrode a molding device when it is added to a synthetic resin and the resulting resin composition is molded.

Another object of the present invention is to provide a phenoxyphosphazene compound which can impart to a molded article of a resin composition containing a synthetic resin, when added thereto, excellent flame retardancy, thermal stability, molding processability and like desired properties.

Another object of the present invention is to provide a process for preparation of such a phenoxyphosphazene compound.

The inventors conducted extensive research to achieve the above objects. Consequently, the inventors found that the desired phenoxyphosphazene compound can be obtained by treating a phenoxyphosphazene compound with a specific adsorbent or specific reagent. The present invention was accomplished based on these findings.

The present invention provides a process for preparation of an improved phenoxyphosphazene compound by treating a phenoxyphosphazene compound with (a) at least one adsorbent selected from activated carbon, silica gel, activated alumina, activated clay, synthetic zeolite and macromolecular adsorbents, or (b) at least one reagent or reactant selected from metal hydrides, hydrazine, hypochlorites, thiosulfates, dialkyl sulfuric acids, ortho esters, diazoalkanes, lactones, alkanesultones, epoxy compounds and hydrogen peroxide or (c) both the adsorbent and reagent.

The present invention provides a process for preparation of an improved phenoxyphosphazene compound by treating a phenoxyphosphazene compound with at least one absorbent selected from activated carbon, silica gel, activated alumina, activated clay, synthetic zeolite and macromolecular adsorbents.

The present invention provides a process for preparation of an improved phenoxyphosphazene compound by treating a phenoxyphosphazene compound with at least one reagent selected from metal hydrides, hydrazine, hypochlorites, thiosulfates, dialkyl sulfuric acids, ortho esters, diazoalkanes, lactones, alkanesultones, epoxy compounds and hydrogen peroxide.

The present invention provides a phenoxyphosphazene which can inhibit the discoloration of a synthetic resin when added thereto.

The present invention provides a phenoxyphosphazene compound which can impart highly improved flame retardancy, thermal stability, molding processability and other properties to a molded article of a resin composition containing the phenoxyphosphazene compound and a synthetic resin.

The present invention provides a phenoxyphosphazene compound which can be added to a synthetic resin without deteriorating the properties of the synthetic resin such as heat resistance, weathering resistance, discoloration resistance, chemical resistance and the like even when the resulting resin composition is stored for a long time.

The present invention provides a phenoxyphosphazene compound which can be added to a polycarbonate resin or a mixture of a polycarbonate resin and another resin without substantially reducing the molecular weight of the polycarbonate resin and changing transparency and the hue such as whiteness of the polycarbonate resin.

The present invention provides a phenoxyphosphazene compound which does not corrode a molding device when a resin composition containing synthetic resin and the phenoxy phosphazene compound is molded.

The present invention provides a flame retardant which contains the above phenoxyphosphazene compound.

The present invention provides a flame-retardant resin composition prepared by adding the above phenoxyphosphazene compound to a synthetic resin.

The present invention provides a flame-retardant resin molded article prepared by molding the above flame-retardant resin composition.

In the present invention, the term "improved" means modifying the properties of a phenoxyphosphazene compound so that the phenoxyphosphazene compound does not deteriorate the properties of a synthetic resin contained in a resin composition when used for the resin composition which is stored for a long time. More specifically, the term "improved" means, for example, lowering the acid value of a phenoxyphosphazene compound to a level less than 0.025.

DETAILED DESCRIPTION OF THE PREFERRED EMBODIMENT

Phenoxyphosphazene Compound

Phenoxyphosphazene compounds which are treated according to the present invention are not limited insofar as they are obtained by the reaction between a dichlorophosphazene compound and a phenol compound or its alkali metal salt, and include a wide variety of known compounds.

Such phenoxyphosphazene compounds include the following:

(1) Cyclic phenoxyphosphazene compounds (hereinafter referred to as "cyclic phenoxyphosphazene compound (1)") represented by formula (1)

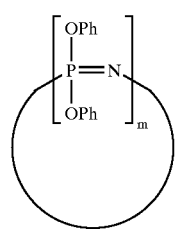

(1)

wherein m is an integer from 3 to 25; and Ph represents a phenyl group.

(2) Chain-like phenoxyphosphazene compounds (hereinafter referred to as "chain-like phenoxyphosphazene compound (2)") represented by formula (2)

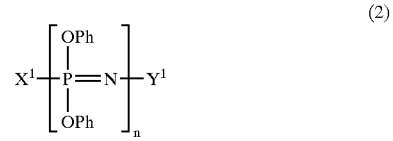

(2)

wherein $X^1$ represents a group $-N=P(OPh)_3$ or a group $-N=P(O)OPh$; $Y^1$ represents a group $-P(OPh)_4$ or a group $-P(O)(OPh)_2$; n is an integer from 3 to 10000; and Ph is as defined above.

(3) Crosslinked phenoxyphosphazene compounds (hereinafter referred to as "crosslinked phenoxyphosphazene compound (3)") obtained by crosslinking at least one phosphazene compound selected from the cyclic phenoxyphosphazene compounds (1) and the chain-like phenoxyphosphazene compounds (2) with at least one crosslinking group selected from o-phenylene group, m-phenylene group, p-phenylene group and a bisphenylene group which is represented by formula (3)

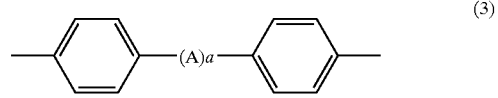

(3)

wherein A represents $-C(CH_3)_2-$, $-SO_2-$, $-S-$ or $-O-$; and a is 0 or 1, the compound (3) having the following characteristics:

(a) each of the crosslinking groups is interposed between two oxygen atoms left after the elimination of phenyl groups of the phosphazene compound;

(b) the amount of the phenyl groups in the crosslinked compound is 50 to 99.9% based on the total amount of the phenyl groups in the phosphazene compound (1) and/or (2); and (c) the crosslinked phenoxyphosphazene compound has no free hydroxyl groups in the molecule.

The terminal groups $X^1$ and $Y^1$ in formula (2) may vary in accordance with the reaction conditions and other factors. When the reaction is carried out under ordinary conditions, e.g., under mild conditions in a non-aqueous system, the resulting product will have a structure wherein $X^1$ is $-N=P(OPh)_3$ and $Y^1$ is $-P(OPh)_4$. When the reaction is carried out under such conditions that water or an alkali metal hydroxide is present in the reaction system, or under so severe conditions that a rearrangement reaction occurs, the resulting product will be a mixture of compounds, some having a structure wherein $X^1$ is $-N=P(OPh)_3$ and $Y^1$ is $-P(OPh)_4$ and others having a structure wherein $X^1$ is $-N=P(O)OPh$ and $Y^1$ is $-P(O)(OPh)_2$.

In this specification, the phrase "to have no free hydroxyl groups in the molecule" means that the amount of free hydroxyl groups is less than the detectable limit, when measured according to the acetylation process using acetic anhydride and pyridine as described on page 353 of "Analytical Chemistry Handbook", revised 3rd edition, Japan Analytical Chemistry Academy, Maruzen Co., (1981). The term "detectable limit" herein means the minimum amount detectable as hydroxyl equivalents per gram of a test sample (crosslinked phenoxyphosphazene compound (3)), more specifically $1 \times 10^{-6}$ hydroxyl equivalents/gram.

On analysis of the crosslinked phenoxyphosphazene compound (3) by the foregoing acetylation process, the resulting amount includes the amount of hydroxyl groups in the residual phenol used as a starting material. Since the quantity of the residual phenol can be determined by high performance liquid chromatography, the amount of only free hydroxyl groups in the crosslinked phenoxyphosphazene compound (3) can be precisely determined.

Among the above phenoxyphosphazene compounds, the cyclic phenoxyphosphazene compound (1) and chain-like phenoxyphosphazene compound (2) are prepared by reacting a dichlorophosphazene compound with an alkali metal phenolate.

Known dichlorophosphazene compounds are useful. Examples are the cyclic dichlorophosphazene compounds (hereinafter referred to as "cyclic dichlorophosphazene compound (4)") represented by formula (4),

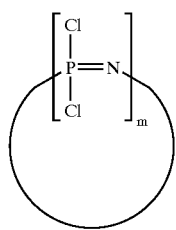

(4)

wherein m is as defined above, the chain-like dichlorophosphazene compounds (hereinafter referred to as "chain-like dichlorophosphazene compound (5)") represented by formula (5),

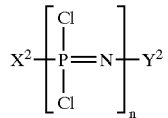

(5)

wherein $X^2$ represents a group —N=PCl$_3$ or group —N=P(O)Cl; $Y^2$ represents a group —P(Cl)$_4$ or group —P(O)Cl$_2$; and n is as defined above, and the like. The dichlorophosphazene compounds may be used singly or in combinations of two or more species. At least one of cyclic dichlorophosphazene compounds and at least one of chain-like dichlorophosphazene compounds may be used in combination.

Dichlorophosphazene compounds can be prepared, for example, by the processes described in H. R. Allcock, "Phosphorus-Nitrogen Compounds", Academic Press, (1972); J. E. Mark, H. R. Allcock, R. West, "Inorganic Polymers", Prentice-Hall International Inc., (1992), etc. For instance, ammonium chloride and phosphorus pentachloride (or ammonium chloride, phosphorus trichloride and chlorine) are reacted in chlorobenzene or tetrachloroethane at about 120 to about 130° C. to remove hydrochloric acid formed, whereby cyclic dichlorophosphazene compounds (4) in which m is 3 to 25 and chain-like dichlorophosphazene compounds (5) in which n is 3 to 25 can be prepared. These dichlorophosphazene compounds (dichlorophosphazene oligomer) are usually obtained as mixtures. The thus obtained mixtures of cyclic and chain-like dichlorophosphazene oligomers are subjected to distillation or recrystallization to be separated into hexachlorocyclotriphosphazene, octachlorocyclotetraphosphazene, decachlorocyclopentaphosphazene and like cyclic dichlorophosphazene compounds. Further, chain-like dichlorophosphazene compounds (5) in which n is from 25 to 10000 can be prepared by heating hexachlorocyclo-triphosphazene to 220 to 250° C. to cause ring-opening polymerization. Cyclic and chain-like dichlorophosphazene compounds each may be used as mixtures or singly after separation.

Known alkali metal phenolates are useful. Examples are alkali metal phenolates (hereinafter referred to as "alkali metal phenolate (6)") represented by formula (6).

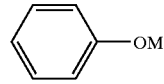

(6)

wherein M represents an alkali metal.

In formula (6), alkali metals represented by M are sodium, potassium, lithium and the like. Examples of alkali metal phenolate (6) are sodium phenolate, potassium phenolate, lithium phenolate and the like. Alkali metal phenolates may be used singly or in combinations of two or more species.

The crosslinked phenoxyphosphazene compound (3) can be prepared, for example, by mixing a dichlorophosphazene compound with an alkali metal phenolate and diphenolate to cause a reaction (first step) and further reacting the resulting compound with an alkali metal phenolate (second step).

Useful dichlorophosphazene compounds include those mentioned above. They may be used in combinations of two or more species, and cyclic and chain-like dichlorophosphazene compounds may be used in combination. Useful alkali metal phenolates include those mentioned above, which may be used in combinations of two or more species.

Known diphenolates can be used. Examples are o-, m- and p-substituted alkali metal diphenolates (hereinafter referred to as "alkali metal diphenolate (7)") represented by formula (7),

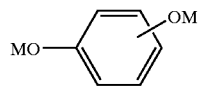

(7)

wherein M is as defined above, alkali metal diphenolates (hereinafter referred to as "alkali metal diphenolate (8)") represented by formula (8),

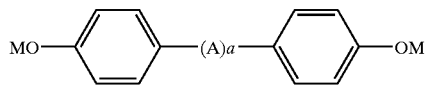

(8)

wherein A, a and M are as defined above, and the like. In the alkali metal diphenolate (7), two groups —O—M (wherein M is as defined above) may positionally in ortho, meta or para relation. Examples of the alkali metal diphenolate (7) are resorcinol, hydroquinone, catechol and like alkali metal salts. Among these, sodium salts and lithium salts are preferable. The alkali metal diphenolate (7) may be used singly or in combinations of two or more species. Examples of the alkali metal diphenolate (8) include 4,4'-isopropylidenediphenol (bisphenol-A), 4,4'-sulfonyldiphenol (bisphenol-S), 4,4'-thiodiphenol, 4,4'-oxydiphenol, 4,4'-diphenol and like alkali metal salts. Among these, sodium salts and lithium salts are preferable. The alkali metal diphenolate (8) may be used singly or in combinations of two or more species. At least one of the alkali metal diphenolate (7) and at least one of the alkali metal diphenolate (8) may be used in combination.

In the first step of the preparation of the crosslinked phosphazene compound (3), it is desirable to use alkali metal phenolate and alkali metal diphenolate in such amounts that not all chlorine atoms in the dichlorophosphazene compound are consumed by the reaction with alkali metal phenolate and alkali metal diphenolate, namely, some chlorine atoms in the dichlorophosphazene compound remain as they are after the reaction with alkali metal phenolate and alkali metal diphenolate. Consequently, —O—M groups (wherein M is as defined above) at both sides in alkali metal diphenolate combine with phosphorus atoms in the dichlorophosphazene compound. In the first step, the total amount of alkali metal phenolate and alkali metal diphenolate used is usually about 0.05 to about 0.9 equivalents, preferably about 0.1 to about 0.8 equivalents, relative to the chlorine content of the dichlorophosphazene compound.

In the second step, it is desirable to use alkali metal phenolate in an amount such that all the chlorine atoms in the compound obtained by the first step can be consumed by the reaction with alkali metal phenolate. The alkali metal phenolate is used usually in an amount of about 1 to about 1.5 equivalents, preferably about 1 to about 1.2 equivalents, relative to the chlorine content of the dichlorophosphazene compound.

The ratio of alkali metal diphenolate (the total amount thereof used in the first and second steps) to alkali metal phenolate (alkali metal diphenolate/alkali metal phenolate, in molar ratio) is usually about 1/2000 to about 1/4, preferably 1/20 to 1/6.

The reactions in the first step and the second step are usually carried out at a temperature ranging from room temperature to about 150° C., preferably about 80 to about 140° C. The reactions are completed usually in about 1 to about 12 hours, preferably about 3 to about 7 hours. These reactions are usually carried out in an organic solvent. Examples of useful organic solvents are aromatic hydrocarbons such as benzene, toluene, xylene, etc.; halogenated aromatic hydrocarbons such as monochlorobenzene, dichlorobenzene, etc.

The decomposition temperature of the crosslinked phenoxyphosphazene compound (3) obtained by the above reactions is usually in the range of 250 to 350° C. The proportion of the phenyl groups in the crosslinked phenoxyphosphazene compound (3) is 50 to 99.9%, preferably 70 to 90%, based on the total amount of the phenyl groups in the cyclic phenoxyphosphazene compound (1) and/or chain-like phenoxyphosphazene compound (2).

Preparation Process A:

In the present invention, the treatment of a phenoxyphosphazene compound using an adsorbent may be conducted in any known manner which can bring the adsorbent and phenoxyphosphazene compound into contact. For example, an adsorbent and a phenoxyphosphazene compound are mixed in a vessel (batch process), or a phenoxyphosphazene compound is passed through an adsorbent filled in a column or a like container.

An adsorbent useful in the present invention is at least one member selected from activated carbon, silica gel, activated alumina, activated clay, synthetic zeolite and macromolecular adsorbents.

Activated carbon, silica gel, activated alumina, activated clay, synthetic zeolite and macromolecular adsorbents can be selected from a wide variety of known products.

Preferable activated carbons are those activated with chemicals and those activated with steam. Activated carbons may be in the shape of cylinders, crushed particles, granules, balls or powder.

Silica gel may be in any shape of minute particles, small particles, medium particles and large granules.

Activated alumina may be acidic, basic or neutral.

Activated clay may be powdery or granular.

Useful synthetic zeolite can be selected from a wide range of commercial products, and may have a pore diameter ranging from about 3 Å to about 10 Å. For example, the pore diameter thereof can be about 3 Å, about 4 Å, about 5 Å and about 10 Å. Synthetic zeolite may be in any form of pellets, beads and a powder.

Useful macromolecular adsorbents include a wide range of known synthetic resins which have an adsorbing ability. Examples include crosslinked polymers which comprise styrene and divinylbenzene, crosslinked polymers which comprises methacrylate ester and ethylene glycol dimethacrylate and the like. Examples of commercially available macromolecular adsorbents include AMBERLITE XAD (trade name, manufactured by ROHM AND HAAS COMPANY), DIAION HP (trade name, manufactured by MITSUBISHI CHEMICAL CORPORATION), etc.

When employing the batch process for carrying out the method of the invention, the amount of an adsorbent used is not limited and may be suitably selected from a wide range depending on the type and amount of the phenoxyphosphazene compound, the type of the adsorbent and other conditions. The amount is usually 1 to 50 parts by weight, preferably 2 to 25 parts by weight, based on 100 parts by weight of the phenoxyphosphazene compound. When the amount of adsorbent added is lower than 1 part by weight, the effect achieved by the adsorbent is likely to be unsatisfactory. When the amount is much higher than 50 parts by weight, the adsorbent adsorbs not only impurities but also phenoxyphosphazene compounds. This may result in a lowered yield.

When the adsorbent is filled in a column and used for treatment, the amount of adsorbent used is not restricted. The adsorbent is placed in a column in an amount suitable for continuous stable column operation, and the adsorbent may be replaced or reactivated when the adsorbing ability of the adsorbent is reduced.

A phenoxyphosphazene compound and an adsorbent are brought into contact in a state that the phenoxyphosphazene compound is melt, or in a state that the phenoxyphosphazene compound is dissolved in a solvent. The solvent may be selected from known solvents which can dissolve the phenoxyphosphazene compound and do not adversely affect the function of the adsorbent.

For example, when a reaction mixture of a dichlorophosphazene compound and an alkali metal phenolate is directly brought into contact with an adsorbent, preferable reaction solvents for the dichlorophosphazene compound and the alkali metal phenolate include aromatic hydrocarbons such as benzene, toluene, xylene, etc., halogenated aromatic hydrocarbons such as monochlorobenzene, dichlorobenzene, etc. When the reaction mixture is diluted, the same solvent same as the above may be used.

When the product isolated from the reaction mixture is dissolved in an organic solvent, solvents to be used include, in addition to the solvents mentioned above, halogenated hydrocarbons such as chloroform, carbon tetrachloride, chloroethane and the like; ketones such as acetone, methyl ethyl ketone, methyl isobutyl ketone and the like; alcohols such as methanol, ethanol, n-propanol, isopropanol, n-butanol, tert-butanol and the like; esters such as methyl formate, ethyl formate, propyl formate, butyl formate, methyl acetate, ethyl acetate, propyl acetate, butyl acetate and the like; ethers such as diethyl ether, diisopropyl ether, dibutyl ether, tetrahydrofuran, dioxane, trioxane and the like; nitrogen-containing hydrocarbons such as acetonitrile, benzonitrile, pyridine and the like.

These solvents may be used singly or in combinations of two or more species. Among these solvents, chloroform, acetone and tetrahydrofuran are preferable.

When the phenoxyphosphazene compound is dissolved in the solvent and treated, the concentration of the phenoxyphosphazene compound is not restricted. However, considering the ease of operation, the concentration is preferably 1 to 90% by weight, more preferably 5 to 80% by weight.

When the phenoxyphosphazene compound is melted and treated, the temperature preferably ranges from the melting point of the phenoxyphosphazene compound to about 200° C. When the phenoxyphosphazene compound is dissolved in the solvent and treated, the treatment may be carried out at any temperature at which the solvent can dissolve the phenoxyphosphazene compound. The temperature usually ranges from 0° C. to the boiling point of the solvent used. A treating time is not restricted because phenoxyphosphazene compound is not adversely affected by contact with the adsorbent for a long time. The treating time is preferably between about 5 minutes to about 12 hours.

Preparation Process B:

The reagent or reactant for use in the present invention is at least one member selected from metal hydrides, hydrazine, hypochlorites, thiosulfates, dialkylsulfuric acids, ortho esters, diazoalkanes, lactones, alkanesultones, epoxy compounds and hydrogen peroxide.

Examples of metal hydrides are lithium aluminum hydride, sodium borohydride and the like. Examples of hypochlorites are potassium hypochlorite, sodium hypochlorite and the like. Examples of thiosulfates are potassium thiosulfate, sodium thiosulfate and the like. Examples of dialkyl sulfuric acids are dimethyl sulfate, diethyl sulfate and the like. Examples of ortho esters are triethyl ortho acetate, triethyl ortho propionate and the like. Examples of diazoalkanes are diazomethane, diazoethane and the like. Examples of lactones are propiolactone, butyrolactone and the like. Examples of alkanesultones are 1,3-propanesultone, 1,4-butanesultone and the like. Examples of epoxy compounds are ethylene oxide, propylene oxide, butylene oxide and the like.

When hydrogen peroxide is used, it is usually used in the form of aqueous solution, having preferably a concentration of 1 to 30% by weight, more preferably a concentration of 5 to 20% by weight.

Among the above reagents, metal hydrides, hypochlorites, thiosulfates and alkanesultones are preferable.

Sodium borohydride is preferable as metal hydride; sodium hypochlorite is preferable as hypochlorite; sodium thiosulfate is preferable as thiosulfate; dimethyl sulfate is preferable as dialkyl sulfuric acid; triethyl ortho acetate is preferable as ortho ester; diazomethane is preferable as diazoalkane; 1,3-propanesultone is preferable as alkanesultone.

The amount of reagent used in the present invention may vary depending on the type of the reagents. For example, a metal hydride is usually used in an amount of 0.5 to 100 parts by weight, preferably 1 to 50 parts by weight, based on 100 parts by weight of the phenoxyphosphazene compound to be treated. When the reagent is a hypochlorite, it is usually used in an amount of 0.5 to 150 parts by weight, preferably 1 to 80 parts by weight, based on 100 parts by weight of the phenoxyphosphazene compound to be treated. When the reagent is a thiosulfate, it is usually used in an amount of 0.5 to 200 parts by weight, preferably about 1 to 100 parts by weight, based on 100 parts by weight of the phenoxyphosphazene compound to be treated. When the reagent is an alkanesultone, it is usually used in an amount of 0.01 to 50 parts by weight, preferably about 0.1 to 30 parts by weight, based on 100 parts by weight of the phenoxyphosphazene compound to be treated.

When the amount of reagent used is too small, improvement of effect is insufficient, whereas when the amount of reagent used is too large, not only a waste of reagent results but also side reactions may occur.

In the treatment of the phenoxyphosphazene compound with the reagent, the phenoxyphosphazene compound in a molten state may be stirred together with the reagent and then separated from the reagent. However, considering low stirring efficiency resulting from high viscosity, difficulty, complicated procedures, etc., of heating and filtration or heating and liquid separation and the like, the phenoxyphosphazene compound is preferably dissolved and treated in an appropriate solvent. In this treatment, any solvent which can dissolve a phenoxyphosphazene compound and does not react with the reagent may be used. Useful solvents are those used in the above treatment by the adsorbent. Among these solvents, benzene, toluene, xylene and monochlorobenzene are preferable.

When the phenoxyphosphazene compound is dissolved in the solvent and the resulting solution is treated with the reagent, the concentration of phenoxyphosphazene compound is not restricted. However, considering the ease of operation, the concentration is preferably 1 to 90% by weight, more preferably 5 to 80% by weight.

The reaction temperature varies depending on the kind of reagents. When the phenoxyphosphazene compound is treated in a molten state, the reaction temperature preferably ranges from about melting point of the phenoxyphosphazene compound to about 200° C. When the phenoxyphosphazene compound dissolved in the solvent is subjected to treatment, the treatement may be carried out at any temperature at which the solvent can dissolve the phenoxyphosphazene compound. Usually, the treatment is conducted at a temperature ranging from 0° C. to the boiling point of the solvent used. A treating time varies depending on the reagent. Generally, it is the range of about 5 minutes to about 12 hours.

In the present invention, the two treatments mentioned above, namely, the treatment with an adsorbent and the treatment with a reagent, may be carried out consecutively or simultaneously.

Phenoxyphosphazene compounds to be treated according to the invention can be used in various forms. For example, the reaction mixture produced by the reaction between a dichlorophosphazene compound and an alkali metal phenolate, etc., may be directly treated; the reaction mixture further diluted with an appropriate organic solvent as mentioned above may be treated; the phenoxyphosphazene compound isolated from the reaction mixture may be melted and treated; the isolated compound which is dissolved in an appropriate organic solvent may be treated; the phenoxyphosphazene compound which has been stored for a long time is melted or dissolved in an appropriate organic solvent and treated.

Among the above phenoxyphosphazene compounds, the crosslinked phenoxyphosphazene compound (3) is preferably used.

The acid value of the phenoxyphosphazene compound purified by the process of the invention is usually lower than 0.025, preferably lower than 0.020, more preferably lower than 0.015, even more preferably lower than 0.010, considering the influence thereof on properties of synthetic resins such as color change, reduced molecular weight, etc.

When compared with an untreated phenoxyphosphazene compound, the phenoxyphosphazene compound treated by the process of the invention is higher in purity and shows less coloration, a lower acid value, less weight loss on heating.

Thus, the present invention provides a process for reducing the acid value of phenoxyphosphazene compound by treating the compound with at least one member selected from adsorbents and reagents.

Flame-Retardant Resin Composition

[Flame Retardant]

The phenoxyphosphazene compound treated by the process of the present invention can be advantageously used as a flame retardant.

[Synthetic Resin]

Synthetic resins to which the modified phenoxyphosphazene compound by the process of the invention can be added are not restricted, and may be any known thermoplastic resin or thermosetting resin.

Examples of thermoplastic resins are polyethylene, polypropylene, polyisoprene, polyester (polyethylene terephthalate, polybutylene terephthalate, etc.), polybutadiene, polystyrene, high-impact polystyrene, acrylonitrile-styrene resin (AS resin), acrylonitrile-butadiene-styrene resin (ABS resin), methyl methacrylate-butadiene-styrene resin (MBS resin), methyl methacrylate-acrylonitrile-butadiene-styrene resin (MABS resin), acrylonitrile-acrylic rubber-styrene resin (AAS resin), polymethyl(meth)acrylate, polycarbonate, polyphenylene ether (PPE), modified polyphenylene ether, polyamide, polyphenylene sulfide, polyimide, polyether ether ketone, polysulfone, polyarylate, polyether ketone, polyether nitrile, polythioether sulfone, polyether sulfone, polybenzimidazole, polycarbodiimide, polyamideimide, polyetherimide, liquid crystalline polymer, etc. Among these, polyester, ABS resin, polycarbonate, modified polyphenylene ether, polyamide, etc., are preferable. Polycarbonate and mixtures of polycarbonate and other resins such as ABS resin, etc., are more preferable.

Thermosetting resins include polyurethane, phenol resin, melamine resin, urea resin, unsatureated polyester resin, diallylphthalate resin, silicon resin, epoxy resin (bisphenol-A epoxy resin, bisphenol-F epoxy resin, bisphenol-AD epoxy resin, phenol novolac epoxy resin, cresol novolac epoxy resin, cyclic aliphatic epoxy resin, glycidyl ester epoxy resin, glycidyl amine epoxy resin, heterocyclic epoxy resin, urethane-modified epoxy resin, brominated bisphenol-A epoxy resin, etc.) and the like. Among these, polyurethane, phenol resin, melamine resin, epoxy resin, etc., are preferable, and epoxy resin is more preferable.

In the present invention, thermoplastic resins and thermosetting resins each may be used singly or in combinations of two or more species. At least one of thermoplastic resins and at least one of thermosetting resins are also used in combination as synthetic resins.

The amount of the phenoxyphosphazene compound purified by the process of the invention is not restricted and can be suitably selected from a wide range depending on various conditions: the type of the synthetic resin to which the compound is added, presence of other additives, the type and amount of other additives, if used, the application of the desired resin composition, etc. However, considering flame retardancy, especially long-term flame retardancy, and the like, the amount is usually about 0.1 to about 100 parts by weight, preferably about 0.5 to about 40 parts by weight, based on 100 parts by weight of a synthetic resin.

[Other Additives]

The rsin composition of the present invention may contain inorganic fillers, fluorocarbon resins, etc., to further enhance its flame retardancy, particularly its ability to prevent dripping (spread of flame caused by dripping of burning resins).

Inorganic fillers and fluorocarbon resins may be used singly, or they may be used simultaneously.

Inorganic fillers have the properties of improving the mechanical strength of resin compositions and enhancing prevention of dripping.

Useful inorganic fillers can be selected from a wide range of resin fillers. Examples are mica, kaolin, talc, silica, clay, barium sulfate, barium carbonate, calcium carbonate, calcium sulfate, calcium silicate, titanium oxide, glass beads, glass balloon, glass flakes, fibrous alkali metal titanates (potassium titanate fibers, sodium titanate fibers, etc.), fibrous borates (aluminum borate fibers, magnesium borate fibers, etc.), zinc oxide fibers, titanium oxide fibers, magnesium oxide fibers, gypsum fibers, aluminum silicate fibers, calcium silicate fibers, silicon carbide fibers, titanium carbide fibers, silicon nitride fibers, titanium nitride fibers, carbon fibers, alumina fibers, alumina-silica fibers, zirconia fibers, quartz fibers, flaked titanate salts, flaked titanium dioxide and the like.

Among these, those having shape anisotropy such as fibrous substances, mica, flaked (or plate-like) titanate salts, flaked titanium oxide, etc., are preferable. Fibrous alkali metal titanates, fibrous borates, zinc oxide fibers, calcium silicate fibers, flaked titanates, flaked titanium oxide, etc., are more preferable.

Inorganic fillers may be used singly or in combinations of two or more species.

The amount of inorganic fillers added is not restricted and is suitably selected from a wide range depending on various conditions: the type of resins added, the amount of a phenoxyphosphazene compound used, the type and amount of other additives used, the use of the resulting resin composition and the like. Considering the balance of the improvement of flame retardancy and the improvement of mechanical characteristics, the amount may be usually about 0.01 to about 50 parts by weight, preferably about 1 to about 20 parts by weight, based on 100 parts by weight of a synthetic resin.

Known fluorocarbon resins can be used. Examples are polytetrafluoroethylene resin (PTFE), tetrafluoroethylene-hexafluoropropylene copolymer (FEP), tetrafluoroethylene-perfluoroalkyl vinyl ether copolymer (PFA), tetrafluoroethylene-ethylene copolymer (ETFE), poly (trifluorochloroethylene) (CTFE), polyfluorovinylidene (PVdF), etc. Among these, PTFE is preferable.

Fluorocarbon resins may be used singly or in combinations of two or more species.

The amount of fluorocarbon resins added is not restricted and is suitably selected from a wide range depending on various conditions: the type of the resin added, the amount of the phenoxyphosphazene compound used, the type and amount of other additives added, the use of the resulting resin composition, etc. The amount may be usually about 0.001 to about 20 parts by weight, preferably about 0.01 to about 5 parts by weight, based on 100 parts by weight of a synthetic resin.

The resin composition of the present invention may further contain various flame retardants in an amount such that they do not deteriorate favorable properties of the resin composition. Known flame retardants are usable without any restriction. Examples are phosphazene compounds other than phenoxyphosphazene compounds, halogen-containing organic phosphorus compounds, halogen-free organic phosphorus compounds, inorganic flame retardants and the like. These may be used singly or in combinations of two or more species.

The resin composition of the present invention may further contain general additives for resin in an amount such that they do not deteriorate favorable properties of the resin composition. Such additives for resin include, but are not limited to, ultraviolet absorbers (benzophenone type, benzotriazole type, cyanoacrylate type, etc.), photostabilizers (hindered amine type, etc.), antioxidants (hindered phenol type, organic phosphorus-type peroxide decomposers, organic sulfur-type peroxide decomposers, etc.), light screens (rutile-type titanium oxide, zinc oxide, chromium oxide, cerium oxide, etc.), metal deactivators (benzotriazole-type, etc.), optical quenching agents (organic nickel, etc.), anti-fogging agents, mildewproofing agents, antibacterial agents, pigments and the like.

The flame-retardant resin composition of the present invention can be prepared by mixing and/or kneading a thermoplastic or thermosetting resin and a phenoxyphosphazene compound, and if needed one or more optional components such as an inorganic filler, a fluorocarbon resin, a flame retardant and or any other additive. These components can be used in a predetermined amount or a situationally appropriate amount, and the preparation can be carried out by any known method. For example, a mixture of these components in the form of a powder, beads, flakes or pellets may be combined and/or mixed using a kneader such as a monoaxial extruder, a biaxial extruder or like extruder, a Banbury mixer, a pressure kneader, a two-roll mill, etc.

[Flame-Retardant Resin Molded Article]

The flame-retardant resin composition of the present invention can be formed into molded articles by a known method, for example, press molding, injection molding, extrusion molding, cast molding, etc. The resin composition can be molded into any shape such as single-layer or multilayer resin plates, sheets, films, balls, blocks, special shapes, etc.

The flame-retardant resin composition of the present invention can find wide application in various fields where synthetic resins are usable: for example, electrical, electronics and telecommunication industries, precision machinery, automobiles and like transportation equipment, fiber products, manufacturing machinery, films for wrapping foods, food containers, products for use in agriculture, forestry and fishery, construction materials, medical goods, furniture parts, etc.

Specific examples of electrical, electronics and telecommunication devices for which molded articles can be used include office and OA equipment such as printers, computers, word processors, keyboards, personal digital assistants (PDA), telephones, cellular phones, facsimile machines, copying machines, electronic cash registers (ECR), desk-top electronic calculators, electronic databooks, electronic dictionaries, cards, holders, stationery, etc.; electrical household appliances such as washing machines, refrigerators, vacuum cleaners, microwave ovens, lighting equipment, game machines, irons, kotatsu (low, covered table with a heat source underneath), etc.; audiovisual equipment such as TV, VTR, video cameras, radio cassette recorders, tape recorders, mini disc players, CD players, speakers, liquid crystal displays, etc.; and electric or electronic parts and telecommunication equipment, such as connectors, relays, condensers, switches, printed circuit boards materials, coil bobbins, semiconductor sealing materials, electric wires, cables, transformers, deflecting yokes, distribution boards, clocks, watches, etc.

Further, the flame-retardant resin moldings of the invention can be widely used for the following applications: materials for automobiles, vehicles, ships, aircraft and constructions, such as chairs, seats (e.g., padding, outer materials), belts, ceiling and wall covering, convertible tops, arm rests, door trims, rear package trays, carpets, mats, sun visors, wheel covers, mattress covers, air bags, insulation materials, hangers, hand straps, electric wire coating materials, electrical insulating materials, paints, coating materials, overlaying materials, floor materials, corner walls, carpets, wall papers, wall covering materials, exterior decorating materials, interior decorating materials, roofing materials, sound insulating panels, thermal insulation panels and window materials; and living necessities and sporting goods such as clothing, curtains, sheets, plywood, laminated fiber boards, carpets, entrance mats, seats, buckets, hoses, containers, glasses, bags, cases, goggles, skies, snowboards, skateboards, rackets, tents and musical instruments.

EFFECT OF THE INVENTION

When added to a synthetic resin, the phenoxyphosphazene compound prepared by the process of the present invention is unlikely to adversely affect the hue (transparency, whiteness, etc.), heat resistance, weathering resistance, chemical resistance, etc., of the synthetic resin.

Especially, when added to a polycarbonate resin or a mixture of a polycarbonate resin and another resin, the phenoxyphosphazene compound prepared by the process of the present invention prevents the polycarbonate resin from decomposition and a decrease in molecular weight, and hardly changes the hue or reduces mechanical characteristics such as impact resistance or other characteristics inherent in the resin such as heat resistance, molding processability, etc.

In addition, a phenoxyphosphazene compound prepared by the process of the present invention has a higher quality, hydrolysis resistance, corrosion resistance, discoloration resistance, etc., and less odor than a phenoxyphosphazene compound washed with an aqueous solution containing an acid or an alkali. A resin composition prepared by adding the phenoxyphosphazene compound of the invention to a synthetic resin can endure severe long-term storage conditions and when molded does not corrode the molding device by which it is molded or cause other problems.

The reason why the present invention can achieve such excellent results not yet fully clarified. However, one of the reasons may be as follows: the treatment of the present invention may efficiently remove or inactivate a trace amount of unreacted materials and impurities having phosphorus residues, amino groups or other groups, etc., which are formed by side reactions during the synthesis of the phenoxyphosphazene compound and adversely affect the properties of the synthetic resin.

BEST MODE FOR CARRYING OUT THE INVENTION

The present invention will be described below in more detail with reference to Examples and Comparative Examples. In the following description, "parts" and "%" mean "weight parts" and "weight %", respectively, unless otherwise specified.

EXAMPLE 1

Synthesis of Phenoxyphosphazene Compound Having p-phenylene-crosslinked Structure A mixture of 103.5 g (1.1 moles) of phenol, 44.0 g (1.1 moles) of sodium hydroxide, 50 g of water and 500 ml of toluene was heated and refluxed and the water was removed from the system, giving a solution of sodium phenolate in toluene.

In parallel with the above reaction, 16.5 g (0.15 moles) of hydroquinone, 94.1 g (1.0 mole) of phenol, 31.1 g (1.3 moles) of lithium hydroxide, 52 g of water and 600 ml of toluene were placed in a 2-liter, 4-necked flask. The mixture was heated and refluxed and only the water was removed from the system, giving a solution of lithium salts of hydroquinone and phenol in toluene. A 20% chlorobenzene solution (580 g) containing 1.0 unit mole (115.9 g) of dichlorophosphazene oligomers (a mixture of 72% of trimer, 17% of tetramer, 7% of pentamer and hexamer, 2% of heptamer and 2% of octamer and higher oligomers) was added dropwise to the toluene solution at 30° C. or lower with stirring, followed by reaction at 110° C. for 3 hours with stirring. To the reaction mixture was added the above prepared toluene solution of sodium phenolate with stirring, and the reaction was allowed to continue at 110° C. for 4 hours.

After the reaction was completed, the reaction mixture was washed three times with 1.0 liter of a 3% aqueous solution of sodium hydroxide and then three times with 1.0 liter of water. The toluene was distilled off under reduced pressure and the reaction mixture was heated and vacuum dried at 120° C. at a pressure of 4 hPa or less for 11 hours. To the solvent-free melt (211 g) was added 10 g of activated clay (trade name: Galleon Earth V2, a product of Mizusawa Industrial Chemicals, Ltd.). The mixture was stirred at 120° C. for 1 hour and heated and filtered to remove the activated clay. The filtrate was cooled, giving 208 g of a white solid.

The crosslinked phenoxyphosphazene compound obtained above had an acid value of 0.008 mgKOH/g and a hydrolyzable chlorine content of 0.02%. The final product had a composition of $[N=P(-O-p-Ph-O-)_{0.15}(-O-Ph)_{1.7}]$, which was confirmed by measurement of phosphorus content and CHN elemental analysis.

This product had a weight average molecular weight (Mw) of 1070 based on a polystyrene standard (GPC analysis). The product did not show a definite melting point and had a decomposition starting temperature of 308° C. and a 5% weight loss temperature of 313° C. as determined by TG/DTA analysis (thermogravimetric analysis).

Further, the quantity of residual hydroxyl groups was found to be below the detection limit of the acetylation method ($1\times10^{-6}$ equivalents/g, as hydroxyl equivalents per gram of the sample).

75 parts of a polycarbonate resin (trade name: lupilon S-2000F, manufactured by Mitsubishi Engineering Plastics Co., Ltd., the same product used below); 25 parts of an ABS resin (trade name: Santac UT-61, a product of Mitsui Chemicals Inc., the same product used below); 0.5 parts of polytetrafluoroethylene (PTFE, trade name: Fluon G307, a product of Asahi Glass Co., Ltd.); and 12.5 parts of the crosslinked phenoxyphosphazene compound obtained above were kneaded using a biaxial extruder and formed into pellets. The pellets were molded into disks with a diameter of 50 mm and a thickness of 1.4 mm using an injection molder.

The change in yellow index (ΔYI) of these disk-shaped samples as compared to the yellow index (YI) of standard disk-shaped samples made from 75 parts of polycarbonate resin, 25 parts of ABS resin and 0.5 parts of PTFE was measured with a color computer (manufactured by Suga Test Instruments Co., Ltd.) and found to be 2.2.

100 parts of the polycarbonate resin, 0.5 parts of PTFE and 5.0 parts of the crosslinked phenoxyphosphazene compound obtained above were kneaded using a biaxial extruder at 270° C. to give pellets. The pellets were dissolved in tetrahydrofuran (THF) and analyzed by GPC. According to the analysis, this product had a weight average molecular weight (Mw) of 55,200 (based on a polystyrene standard). A kneaded product of 100 parts of the polycarbonate resin and 0.5 parts of PTFE had a weight average molecular weight (Mw) of 55,400 (based on a polystyrene standard).

These results show that use of the crosslinked phenoxyphosphazene compound makes little difference to the weight average molecular weight of the polycarbonate resin, which indicates that decomposition of the polycarbonate resin is inhibited.

EXAMPLE 2

Synthesis of Phenoxyphosphazene Compound Having p-phenylene-crosslinked Structure A solvent-free melt was prepared in the same manner as in Example 1. The melt was then dissolved in a mixed solvent of 1.0 liter of tetrahydrofuran and 0.1 liter of methanol. After addition of 21 g of sodium borohydride, the mixture was stirred at room temperature for 24 hours.

After the reaction was completed, the reaction mixture was neutralized with 2.5% hydrochloric acid and the organic layer was concentrated under reduced pressure. The solid was dissolved in 1.0 liter of toluene and washed twice with a 2.5% aqueous solution of sodium hydroxide, once with 2.5% hydrochloric acid, once with a 5% aqueous solution of sodium hydrogencarbonate, and twice with a 2% aqueous solution of sodium sulfate. The organic layer was concentrated under reduced pressure. The resulting product was heated and vacuum dried at 80° C. at a pressure of 4 hPa or less for 11 hours, giving 202 g of a white solid.

The crosslinked phenoxyphosphazene compound obtained above had an acid value of 0.009 mgKOH/g and a hydrolyzable chlorine content of 0.02%. The final product had a composition of $[N=P(-O-p-Ph-O-)_{0.15}(-O-Ph)_{1.7}]$, which was confirmed by measurement of phosphorus content and CHN elemental analysis.

This product had a weight average molecular weight (Mw) of 1070 based on a polystyrene standard (GPC analysis). The product did not show a definite melting point and had a decomposition starting temperature of 308° C. and a 5% weight loss temperature of 313° C. as determined by TG/DTA analysis.

Further, the quantity of residual hydroxyl groups was found to be below the detection limit of the acetylation method.

75 parts of the polycarbonate (hereinafter referred to as "PC") resin (Iupilon S-2000F), 25 parts of the ABS resin (Santac UT-61), 0.5 parts of PTFE and 12.5 parts of the crosslinked phenoxyphosphazene compound obtained above were kneaded using a biaxial extruder and formed into pellets. The pellets were molded into disks with a diameter of 50 mm and a thickness of 1.4 mm using an injection molder.

The change in yellow index (ΔYI) of these disk-shaped samples was measured with a color computer (manufactured by Suga Test Instruments Co., Ltd.) and found to be 2.4.

100 parts of PC resin, 0.5 parts of PTFE and 5.0 parts of the crosslinked phenoxyphosphazene compound were kneaded at 270° C. using a biaxial extruder and formed into pellets. The pellets were dissolved in THF and analyzed by GPC. According to the analysis, this product had a weight average molecular weight (Mw) of 55,100 (based on a polystyrene standard). A kneaded product of 100 parts of PC resin and 0.5 parts of PTFE had a weight average molecular weight (Mw) of 55,400 (based on a polystyrene standard).

These results show that use of the crosslinked phenoxyphosphazene compound makes little difference to the weight average molecular weight of PC resin, which indicates that the decomposition of PC resin is inhibited.

COMPARATIVE EXAMPLE 1

Synthesis of Phenoxyphosphazene Compound Having p-phenylene-crosslinked Structure A phenoxyphosphazene compound was prepared in the same manner as in Example 1 except that activated clay was not added after completion of the reaction. A slightly yellow solid (211 g) was obtained.

The crosslinked phenoxyphosphazene compound thus obtained had an acid value of 0.039 mgKOH/g and a hydrolyzable chlorine content of 0.04%. The final product had a composition of $[N=P(-O-p-Ph-O-)_{0.15}(-O-Ph)_{1.7}]$, which was confirmed by measurement of phosphorus content and CHN elemental analysis.

This product had a weight average molecular weight (Mw) of 1080 based on a polystyrene standard (GPC analysis). The product did not show a definite melting point and had a decomposition starting temperature of 306° C. and a 5% weight loss temperature of 311° C. as determined by TG/DTA analysis. The quantity of residual hydroxyl groups was found to be below the detection limit of the acetylation method.

75 parts of PC resin, 25 parts of ABS resin, 0.5 parts of PTFE and 12.5 parts of the crosslinked phenoxyphosphazene compound obtained above were kneaded using a biaxial extruder and formed into pellets. The pellets were molded into disks with a diameter of 50 mm and a thickness of 1.4 mm using an injection molder. The change in yellow index (ΔYI) of these disk-shaped samples was found to be 5.2.

100 parts of PC resin, 0.5 parts of PTFE and 5.0 parts of the crosslinked phenoxyphosphazene compound were kneaded at 270° C. using a biaxial extruder and formed into pellets. The pellets were dissolved in THF and analyzed by GPC. According to the analysis, this product had a weight average molecular weight (Mw) of 54,800 (based on a polystyrene standard). A kneaded product of 100 parts of PC resin and 0.5 parts of PTFE had a weight average molecular weight (Mw) of 55,400 (based on a polystyrene standard).

These results show that use of the crosslinked phenoxyphosphazene compound reduces the weight average molecular weight of PC resin, which indicates the decomposition of PC resin.

EXAMPLE 3

(Synthesis of Phenoxyphosphazene Compound Having 2,2-bis(p-oxyphenyl)isopropyridene-crosslinked Structure 65.9 g (0.7 moles) of phenol and 500 ml of toluene were placed in a 1-liter, 4-necked flask. While stirring the mixture and maintaining the internal temperature at 25° C., 14.9 g (0.65 gram atoms) of finely cut metallic sodium were added. After completion of the addition, stirring was continued for 8 hours at 77° C. to 113° C. until the metallic sodium was completely consumed.

In parallel with the above reaction, 57.1 g (0.25 moles) of bisphenol-A, 103.5 g (1.1 moles) of phenol and 800 ml of THF were placed in a 3-liter, 4-necked flask. While stirring the mixture and maintaining the internal temperature at 25° C., 11.1 g (1.6 gram atoms) of finely cut metallic lithium were added. After completion of the addition, stirring was continued for 8 hours at 61° C. to 68° C. until the metallic lithium was completely consumed. While stirring the mixture and maintaining the internal temperature at 20° C. or lower, 1.0 unit mole (115.9 g) of dichlorophosphazene oligomers (concentration 37%, monochlorobenzene solution 313 g, a mixture of 72% of trimer, 17% of tetramer, 7% of pentamer and hexamer, 2% of heptamer and 2% of octamer and higher oligomers) was added dropwise to the resulting slurry solution over a period of 1 hour, followed by reaction at 80° C. for 2 hours. Subsequently, while stirring the mixture and maintaining the internal temperature at 20° C., the sodium phenolate solution prepared above was added to the reaction mixture over a period of 1 hour, followed by reaction at 80° C. for 5 hours.

After the reaction was completed, the reaction mixture was concentrated to remove THF, and 1 liter of toluene was added to the concentrate. The resulting toluene solution was washed three times with 1 liter of a 2% aqueous solution of sodium hydroxide and then three times with 1 liter of water. The solution was passed through a column containing 50 g of activated alumina (a product of Wako Pure Chemical Industries, Ltd.) at room temperature. The resulting organic layer was concentrated under reduced pressure. The resulting product was heated and vacuum dried at 80° C. at a pressure of 4 hPa or less for 11 hours, giving 227 g of a white solid.

The crosslinked phenoxyphosphazene compound thus obtained had an acid value of 0.007 mgKOH/g and a hydrolyzable chlorine content of 0.03%. This product had an approximate composition of $[N=P(-O-Ph-C(CH_3)_2-Ph-O-)_{0.25}(-O-Ph)_{1.50}]$, which was confirmed by measurement of phosphorus content and CHN elemental analysis.

This product had a weight average molecular weight (Mw) of 1120 based on a polystyrene standard (GPC analysis). The product did not show a definite melting point and had a decomposition starting temperature of 310° C. and a 5% weight loss temperature of 316° C. as determined by TG/DTA analysis. The quantity of residual hydroxyl groups was found to be below the detection limit of the acetylation method.

75 parts of PC resin, 25 parts of ABS resin, 0.5 parts of PTFE and 12.5 parts of the crosslinked phenoxyphosphazene compound obtained above were kneaded using a biaxial extruder and formed into pellets. The pellets were molded into disks with a diameter of 50 mm and a thickness of 1.4 mm using an injection molder. The change in yellow index (ΔYI) of these disk-shaped samples was found to be 2.3.

100 parts of PC resin, 0.5 parts of PTFE and 5.0 parts of the crosslinked phenoxyphosphazene compound were kneaded at 270° C. using a biaxial extruder and formed into pellets. The pellets were dissolved in THF and analyzed by GPC. According to the analysis, this product had a weight average molecular weight (Mw) of 55,100 (based on a polystyrene standard). A kneaded product of 100 parts of PC resin and 0.5 parts of PTFE had a weight average molecular weight (Mw) of 55,400 (based on a polystyrene standard).

These results show that use of the crosslinked phenoxyphosphazene compound makes little difference to the weight average molecular weight of PC resin, which indicates the decomposition of PC resin is inhibited.

EXAMPLE 4

Synthesis of Phenoxyphosphazene Compound Having 2,2-bis(p-oxyphenyl)isopropyridene-crosslinked Structure A phenoxyphosphazene compound was prepared in the same manner as in Example 3 except for the following differences in the production process:

(a) after completion of the reaction, the reaction mixture was concentrated to remove THF and 1 liter of toluene was added;
(b) the toluene solution was then washed three times with 0.5 liters of a 5% aqueous solution of sodium thiosulfate and three times with a 2% aqueous solution of sodium sulfate and the organic layer was concentrated under reduced pressure; and
(c) the resulting product was heated and vacuum dried at 80° C. at a pressure of 4 hPa or less for 11 hours.

As a result, 220 g of a white solid was obtained.

The crosslinked phenoxyphosphazene compound thus obtained had an acid value of 0.008 mgKOH/g and a hydrolyzable chlorine content of 0.03%. The final product had a composition of [N=P(—O—Ph—C(CH$_3$)$_2$—Ph—O—)$_{0.25}$(—O—Ph)$_{1.50}$], which was confirmed by measurement of phosphorus content and CHN elemental analysis.

This product had a weight average molecular weight (Mw) of 1120 based on a polystyrene standard (GPC analysis). The product did not show a definite melting point and had a decomposition starting temperature of 309° C. and a 5% weight loss temperature of 315° C. as determined by TG/DTA analysis.

Further, the quantity of residual hydroxyl groups was found to be below the detection limit of the acetylation method.

75 parts of PC resin, 25 parts of ABS resin, 0.5 parts of PTFE and 12.5 parts of the crosslinked phenoxyphosphazene compound were kneaded using a biaxial extruder and formed into pellets. The pellets were molded into disks with a diameter of 50 mm and a thickness of 1.4 mm using an injection molder. The change in yellow index (ΔYI) of these disk-shaped samples was found to be 2.6.

100 parts of PC resin, 0.5 parts of PTFE and 5.0 parts of the crosslinked phenoxyphosphazene compound were kneaded at 270° C. using a biaxial extruder and formed into pellets. The pellets were dissolved in THF and analyzed by GPC. According to the analysis, this product had a weight average molecular weight (Mw) of 55,000 (based on a polystyrene standard). A kneaded product of 100 parts of PC resin and 0.5 parts of PTFE had a weight average molecular weight (Mw) of 55,400 (based on a polystyrene standard).

These results show that use of the crosslinked phenoxyphosphazene compound makes little difference to the weight average molecular weight of PC resin, which indicates that the decomposition of PC resin is inhibited.

COMPARATIVE EXAMPLE 2

Synthesis of Phenoxyphosphazene Compound Having 2,2-bis(p-oxyphenyl)isopropyridene-crosslinked Structure A phenoxyphosphazene compound was prepared in the same manner as in Example 3 except that activated alumina was not added after completion of the reaction. A slightly yellow solid (229 g) was obtained.

The crosslinked phenoxyphosphazene compound thus obtained had an acid value of 0.035 mgKOH/g and a hydrolyzable chlorine content of 0.07%. The final product had a composition of [N=P(—O—Ph—C(CH$_3$)$_2$—Ph—O—)$_{0.25}$(—O—Ph)$_{1.50}$], which was confirmed by measurement of phosphorus content and CHN elemental analysis.

This product had a weight average molecular weight (Mw) of 1130 based on a polystyrene standard (GPC analysis). The product did not show a definite melting point and had a decomposition starting temperature of 308° C. and a 5% weight loss temperature of 313° C. as determined by TG/DTA analysis. The quantity of residual hydroxyl groups was found to be below the detection limit of the acetylation method.

75 parts of PC resin, 25 parts of ABS resin, 0.5 parts of PTFE and 12.5 parts of the crosslinked phenoxyphosphazene compound obtained above were kneaded using a biaxial extruder and formed into pellets. The pellets were molded into disks with a diameter of 50 mm and a thickness of 1.4 mm using an injection molder. The change in yellow index (ΔYI) of these disk-shaped samples was found to be 5.6.

100 parts of PC resin, 0.5 parts of PTFE and 5.0 parts of the crosslinked phenoxyphosphazene compound were kneaded at 270° C. using a biaxial extruder and formed into pellets. The pellets were dissolved in THF and analyzed by GPC. According to the analysis, this product had a weight average molecular weight (Mw) of 54,700 (based on a polystyrene standard). A kneaded product of 100 parts of PC resin and 0.5 parts of PTFE had a weight average molecular weight (Mw) of 55,400 (based on a polystyrene standard).

These results show that use of the crosslinked phenoxyphosphazene compound reduces the weight average molecular weight of PC resin, which indicates the decomposition of PC resin.

EXAMPLE 5

Synthesis of Phenoxyphosphazene Compound Having 4,4'-sulfonyldiphenylene(Bisphenol-S Residue)-crosslinked Structure 37.6 g (0.4 moles) of phenol and 500 ml of THF were placed in a 1-liter, 4-necked flask. While stirring the mixture and maintaining the internal temperature at 25° C., 9.2 g (0.45 gram atoms) of finely cut metallic sodium were added. After completion of the addition, stirring was continued for 5 hours at 65° C. to 72° C. until the metallic sodium was completely consumed, to thereby prepare a mixed solution A of sodium phenolate.

In parallel with the above reaction, 160.0 g (1.70 moles) of phenol and 12.5 g (0.05 moles) of bisphenol-S were dissolved in 500 ml of THF in a 1-liter, 4-necked flask, and 41.4 g (1.8 gram atoms) of metallic sodium was added at 25° C. or lower. After completion of the addition, the temperature was elevated to 61° C. over a period of 1 hour, and stirring was continued for 6 hours at 61° C. to 68° C. to give a mixed solution B of sodium phenolate. This solution was added dropwise to 580 g of a 20% chlorobenzene solution containing 1.0 unit mole (115.9 g) of dichlorophosphazene oligomers (a mixture of 72% of trimer, 17% of tetramer, 7% of pentamer and hexamer, 2% of heptamer, 2% of octamer and higher oligomers) with cooling at 25° C. or lower and stirring, and the reaction was allowed to proceed at 71° C. to 73° C. for 5 hours. Then, the mixed solution A of sodium phenolate prepared above was added to the reaction mixture, and the reaction was allowed to continue at 71° C. to 73° C. for 3 hours.

After completion of the reaction, the reaction mixture was concentrated and dissolved again in 500 ml of chlorobenzene. The solution was washed three times with a 5% aqueous solution of sodium hydroxide, once with 5% sulfuric acid, once with a 5% aqueous solution of sodium bicarbonate and three times with water. Then 10 g of activated carbon (Carboraffin, a product of Takeda Chemical Industries, Ltd.) was added and stirred at room temperature for 1 hour. The activated carbon was separated by filtration and the organic layer was concentrated and dried, giving 216 g of a white solid.

The crosslinked phenoxyphosphazene compound obtained above had an acid value of 0.006 mgKOH/g and a hydrolyzable chlorine content of 0.01% or less. This product had an approximate composition of [N=P(—O—Ph—$SO_2$—Ph—O—)$_{0.05}$(—O—Ph)$_{1.90}$], which was confirmed by measurement of phosphorus content and CHN elemental analysis.

The product had a weight average molecular weight (Mw) of 1070 based on a polystyrene standard. This product had a melting point (Tm) of 106° C., a decomposition starting temperature of 323° C. and a 5% weight loss temperature of 337° C. as determined by TG/DTA analysis. The quantity of residual hydroxyl groups was below the detection limit of the acetylation method.

75 parts of PC resin, 25 parts of ABS resin, 0.5 parts of PTFE and 12.5 parts of the crosslinked phenoxyphosphazene compound were kneaded using a biaxial extruder and formed into pellets. The pellets were molded into disks with a diameter of 50 mm and a thickness of 1.4 mm using an injection molder. The change in yellow index (ΔYI) of these disk-shaped samples was found to be 2.0.

100 parts of PC resin, 0.5 parts of PTFE and 5.0 parts of the crosslinked phenoxyphosphazene compound were kneaded at 270° C. using a biaxial extruder and formed into pellets. The pellets were dissolved in THF and analyzed by GPC. According to the analysis, this product had a weight average molecular weight (Mw) of 55,200 (based on a polystyrene standard). A kneaded product of 100 parts of PC resin and 0.5 parts of PTFE had a weight average molecular weight (Mw) of 55,400 (based on a polystyrene standard).

These results show that use of the crosslinked phenoxyphosphazene compound makes little difference to the weight average molecular weight of PC resin, which indicates the decomposition of PC resin is inhibited.

EXAMPLE 6

Synthesis of Phenoxyphosphazene Compound Having 4,4'-sulfonyldiphenylene(Bisphenol-S Residue)-crosslinked Structure As in Example 5, the mixed solution B of sodium phenolate was added dropwise to the chlorobenzene solution containing dichlorophosphazene oligomers with cooling at 25° C. or lower and stirring, and the reaction was allowed to proceed at 71° C. to 73° C. with stirring for 5 hours. Then, the mixed solution A of sodium phenolate was added to the reaction mixture, and the reaction was allowed to continue at 71° C. to 73° C. for 3 hours.

After the reaction was completed, 25 g of a 50% aqueous solution of potassium hydroxide was added. While stirring the mixture at 120° C., 25 g of 1,3-propanesultone was slowly added dropwise. Stirring was continued at 120° C. for another 2 hours. The reaction mixture was washed three times with a 5% aqueous solution of sodium bicarbonate and twice with a 2% aqueous solution of sodium sulfate and concentrated and dried, giving 211 g of a white solid.

The crosslinked phenoxyphosphazene compound obtained above had an acid value of 0.008 mgKOH/g and a hydrolyzable chlorine content of 0.01% or less. This product had an approximate composition of [N=P(—O—Ph—$SO_2$—Ph-O—)$_{0.05}$(—O—Ph)$_{1.90}$], which was confirmed by measurement of phosphorus content and CHN elemental analysis.

The product had a weight average molecular weight (Mw) of 1070 based on a polystyrene standard. This product had a melting point (Tm) of 106° C., a decomposition starting temperature of 322° C. and a 5% weight loss temperature of 337° C. as determined by TG/DTA analysis. The quantity of residual hydroxyl groups was found to be below the detection limit of the acetylation method.

75 parts of PC resin, 25 parts of ABS resin, 0.5 parts of PTFE and 12.5 parts of the crosslinked phenoxyphosphazene compound were kneaded using a biaxial extruder and formed into pellets. The pellets were molded into disks with a diameter of 50 mm and a thickness of 1.4 mm using an injection molder. The change in yellow index (ΔYI) of this disk-shaped sample was found to be 2.1.

100 parts of PC resin, 0.5 parts of PTFE and 5.0 parts of the crosslinked phenoxyphosphazene compound were kneaded at 270° C. using a biaxial extruder and formed into pellets. The pellets were dissolved in THF and analyzed by GPC. According to the analysis, this product had a weight average molecular weight (Mw) of 55,200 (based on a polystyrene standard). A kneaded product of 100 parts of PC resin and 0.5 parts of PTFE had a weight average molecular weight (Mw) of 55,400 (based on a polystyrene standard).

These results show that use of the crosslinked phenoxyphosphazene compound makes little difference to the weight average molecular weight of PC resin, which indicates that the decomposition of PC resin is inhibited.

COMPARATIVE EXAMPLE 3

Synthesis of Phenoxyphosphazene Compound Having 4,4'-sulfonyldiphenylene(Bisphenol-S Residue)-crosslinked Structure A phenoxyphosphazene compound was prepared in the same manner as in Example 5 except that activated carbon was not added after completion of the reaction. A light yellow solid (218 g) was obtained.

The crosslinked phenoxyphosphazene compound obtained above had an acid value of 0.032 mgKOH/g and a hydrolyzable chlorine content of 0.01% or less. This product had an approximate composition of [N=P(—O—Ph—$SO_2$—Ph—O—)$_{0.05}$(—O—Ph)$_{1.90}$], which was confirmed by measurement of phosphorus content and CHN elemental analysis.

The product had a weight average molecular weight (Mw) of 1080 based on a polystyrene standard. This product had a melting point (Tm) of 103° C., a decomposition starting temperature of 320° C. and a 5% weight loss temperature of 334° C. as determined by TG/DTA analysis. The quantity of residual hydroxyl groups was found to be below the detection limit of the acetylation method.

75 parts of PC resin, 25 parts of ABS resin, 0.5 parts of PTFE and 12.5 parts of the crosslinked phenoxyphosphazene compound obtained above were kneaded using a biaxial extruder and formed into pellets. The pellets were molded into disks with a diameter of 50 mm and a thickness of 1.4 mm using an injection molder. The change in yellow index (ΔYI) of these disk-shaped samples was found to be 5.1.

100 parts of PC resin, 0.5 parts of PTFE and 5.0 parts of the crosslinked phenoxyphosphazene compound were kneaded at 270° C. using a biaxial extruder and formed into pellets. The pellets were dissolved in THF and analyzed by GPC. According to the analysis, this product had a weight average molecular weight (Mw) of 54,700 (based on a polystyrene standard). A kneaded product of 100 parts of PC resin and 0.5 parts of PTFE had a weight average molecular weight (Mw) of 55,400 (based on a polystyrene standard).

These results show that use of the crosslinked phenoxyphosphazene compound reduces the weight average molecular weight of PC resin, which indicates the decomposition of PC resin.

EXAMPLE 7

Synthesis of Phenoxyphosphazene Compound 123.0 g (1.3 moles) of phenol was placed into a 1-liter, 4-necked flask equipped with a stirrer, a thermometer and a reflux condenser, and 500 ml of THF was added to give a uniform solution. Then 27.6 g of sodium metal was added at 25° C. or lower and the mixture was heated to 61° C. over a period of 1 hour and stirring was continued at 61° C. to 68° C. for 6 hours to give a sodium phenolate solution.

In parallel with the above reaction, a solution of 58 g (0.5 unit moles) of a mixture of hexachlorocyclotriphosphazene and octachlorocyclotetraphosphazene (76% of trimer and 24% of tetramer) in 250 ml of THF was placed into a 2-liter, 4-necked flask, and the sodium phenolate solution prepared above was added dropwise with stirring at 25° C. or lower. After dropwise addition, the reaction was allowed to proceed with stirring at 71° C. to 73° C. for 15 hours.

After the reaction was completed, the reaction mixture was concentrated and the concentrate was dissolved again in 500 ml of toluene. This solution was washed once with water, three times with a 5% aqueous solution of sodium hydroxide, once with 5% sulfuric acid, once with a 5% aqueous solution of sodium bicarbonate and once with water. Then 10 g of silica gel (trade name: Wako gel C-200, a product of Wako Pure Chemical Industries, Ltd.) was added to the toluene solution and the mixture was stirred at room temperature for 1 hour. After the silica gel was separated by filtration, the organic layer was concentrated under reduced pressure and the concentrate was heated and vacuum dried at 80° C. at a pressure of 4 hPa or less for 11 hours, giving 102 g of a white solid.

The crosslinked phenoxyphosphazene compound obtained above had an acid value of 0.010 mgKOH/g and a hydrolyzable chlorine content of 0.03% or less. This product had a melting point (Tm) of 109° C., a decomposition starting temperature of 326° C. and a 5% weight loss temperature of 340° C. as determined by TG/DTA analysis. The quantity of residual hydroxyl groups was found to be below the detection limit of the acetylation method.

75 parts of PC resin, 25 parts of ABS resin, 0.5 parts of PTFE and 12.5 parts of the crosslinked phenoxyphosphazene compound obtained above were kneaded using a biaxial extruder and formed into pellets. The pellets were molded into disks with a diameter of 50 mm and a thickness of 1.4 mm using an injection molder. The change in yellow index ($\Delta$YI) of this disk-shaped sample was 2.3.

100 parts of PC resin, 0.5 parts of PTFE and 5.0 parts of the phenoxyphosphazene compound were kneaded at 270° C. using a biaxial extruder and formed into pellets. The pellets were dissolved in THF and analyzed by GPC. According to the analysis, this product had a weight average molecular weight (Mw) of 55,000 (based on a polystyrene standard). A kneaded product of 100 parts of PC resin and 0.5 parts of PTFE had a weight average molecular weight (Mw) of 55,400 (based on a polystyrene standard).

These results show that use of the crosslinked phenoxyphosphazene compound makes little difference to the weight average molecular weight of PC resin, which indicates that the decomposition of PC resin is inhibited.

COMPARATIVE EXAMPLE 4

Synthesis of Phenoxyphosphazene Compound

A phenoxyphosphazene compound was prepared in the same manner as in Example 7 except that silica gel was not added after completion of the reaction. A slightly yellow solid (109 g) was obtained.

This crosslinked phenoxyphosphazene compound had an acid value of 0.045 mgKOH/g and a hydrolyzable chlorine content of 0.08%. This product had a melting point (Tm) of 107° C., a decomposition starting temperature of 324° C. and a 5% weight loss temperature of 338° C. as determined by TG/DTA analysis. The quantity of residual hydroxyl groups was found to be below the detection limit of the acetylation method.

75 parts of PC resin, 25 parts of ABS resin, 0.5 parts of PTFE and 12.5 parts of the crosslinked phenoxyphosphazene compound obtained above were kneaded using a biaxial extruder and formed into pellets. The pellets were molded into disks with a diameter of 50 mm and a thickness of 1.4 mm using an injection molder. The change in yellow index ($\Delta$YI) of these disk-shaped samples was found to be 6.4.

100 parts of PC resin, 0.5 parts of PTFE and 5.0 parts of the crosslinked phenoxyphosphazene compound were kneaded using a biaxial extruder and formed into pellets. The pellets were dissolved in THF and analyzed by GPC. According to the analysis, this product had a weight average molecular weight (Mw) of 53,500 (based on a polystyrene standard). A kneaded product of 100 parts of PC resin and 0.5 parts of PTFE had a weight average molecular weight (Mw) of 55,400 (based on a polystyrene standard).

These results show that use of the crosslinked phenoxyphosphazene compound reduces the weight average molecular weight of PC resin, which indicates the decomposition of PC resin.

The results of Examples 1–7 and Comparative Examples 1–4 clearly show that use of the phosphazene compounds of the invention does not adversely affect the hue (whiteness) of synthetic resin, especially a mixture of PC resin and ABS resin.

EXAMPLES 8–14 AND COMPARATIVE EXAMPLES 5–8

The various synthetic resins shown in Table 1, the phenoxyphosphazene compounds obtained in Examples 1–7 and Comparative Examples 1–4, and PTFE were mixed in the amounts shown in Table 1 to give resin compositions of the invention and comparative resin compositions.

PTFE, PC resin and ABS resin are as described in Example 1. The other synthetic resins are as follows:

PBT: trade name "Torecon 1200S", a product of Toray Industries, Inc.
m-PPE: trade name "Xyron X-9108", a product of Asahi Kasei corporation.

The physical properties of the prepared resin compositions were tested in the following manner.

Flame retardancy (UL94V): samples 1.6 mm in thickness were evaluated by according to the UL94V standard.
Melt flow rate (MFR): MFR was measured according to JIS K 7210 under the following conditions:
Condition 1: 21.18N (2.16 kgf), 280° C.
Condition 2: 37.26N (3.80 kgf), 230° C.
Condition 3: 21.18N (2.16 kgf), 275° C.
Heat distortion temperature (HDT): samples 4 mm in thickness were evaluated at 1.82 MPa (18.5 kgf/cm$^2$) according to JIS K 7191.
Impact resistance (IZOD): Izod impact strength of notched samples 4.1 mm in thickness was measured according to JIS K 7110.
Table 1 shows the results.

TABLE 1

|  | Examples | | | | | | Comparative Examples | | | | |
| --- | --- | --- | --- | --- | --- | --- | --- | --- | --- | --- | --- |
|  | 8 | 9 | 10 | 11 | 12 | 13 | 14 | 5 | 6 | 7 | 8 |
| PC | 100 | 100 | 75 | 75 | 70 | 70 |  | 100 | 75 | 70 |  |
| ABS |  |  | 25 | 25 |  |  |  |  | 25 |  |  |
| PBT |  |  |  |  | 30 | 30 |  |  |  | 30 |  |
| m-PPE |  |  |  |  |  |  | 100 |  |  |  | 100 |
| PTFE | 0.5 | 0.5 | 0.5 | 0.5 | 0.5 | 0.5 | 0.5 | 0.5 | 0.5 | 0.5 | 0.5 |
| Phenoxyphosphazene compound |  |  |  |  |  |  |  |  |  |  |  |
| Example 1 | 5 |  |  |  |  |  |  |  |  |  |  |
| Example 2 |  | 5 |  |  |  |  |  |  |  |  |  |
| Example 3 |  |  | 12.5 |  |  |  |  |  |  |  |  |
| Example 4 |  |  |  | 12.5 |  |  |  |  |  |  |  |
| Example 5 |  |  |  |  | 10 |  |  |  |  |  |  |
| Example 6 |  |  |  |  |  | 10 |  |  |  |  |  |
| Example 7 |  |  |  |  |  |  | 7.5 |  |  |  |  |
| Comparative Example 1 |  |  |  |  |  |  |  | 5 |  |  |  |
| Comparative Example 2 |  |  |  |  |  |  |  |  | 12.5 |  |  |
| Comparative Example 3 |  |  |  |  |  |  |  |  |  | 10 |  |
| Comparative Example 4 |  |  |  |  |  |  |  |  |  |  | 7.5 |
| Flame retardancy (UL94V) | V-0 | V-0 | V-0 | V-0 | V-0 | V-0 | V-0 | V-0 | V-0 | V-0 | V-0 |
| Melt flow rate (g/10 min.) | 23 | 23 | 12 | 12 | 57 | 57 | 3 | 24 | 13 | 58 | 3 |
| Condition (number) | 1 | 1 | 2 | 2 | 1 | 1 | 3 | 1 | 2 | 1 | 3 |
| Heat distortion temperature (° C.) | 120 | 120 | 94 | 94 | 94 | 94 | 132 | 118 | 93 | 92 | 130 |
| Impact resistance (J/m) | 103 | 102 | 186 | 185 | 57 | 57 | 288 | 100 | 175 | 54 | 261 |

The above results clearly show that compared to a molding made of a resin composition containing an untreated phenoxyphosphazene compound, a molding made of a resin composition containing a phenoxyphosphazene compound treated by the method of the present invention has equivalent or superior flame retardancy, heat resistance and mechanical properties.

What is claimed is:

1. A method for preparation of an improved phenoxyphosphazene compound, comprising treating a phenoxyphosphazene compound with (a) at least one adsorbent selected from activated carbon, silica gel, activated alumina, activated clay, synthetic zeolite and macromolecular adsorbents, (b) at least one reagent selected from metal hydrides, hydrazine, hypochlorites, thiosulfates, dialkyl sulfuric acids, ortho esters, diazoalkanes, lactones, alkanesultones, epoxy compounds and hydrogen peroxide, or (c) both the adsorbent and reagent, thereby reducing the acid value of said phosphazene compound to lower than 0.025 mgKOH/g.

2. The method according to claim 1, wherein the phosphazene compound is at least one compound selected from (1) cyclic phenoxyphosphazene compound represented by formula

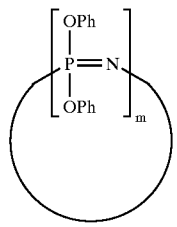

(1)

wherein m is an integer from 3 to 25 and Ph represents a phenyl group;

(2) chain-like phenoxyphosphazene compound represented by formula

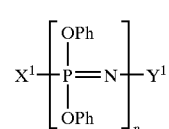

(2)

wherein $X^1$ represents a group —N=P(OPh)$_3$ or a group —N=P(O)OPh, $Y^1$ represents a group —P(OPh)$_4$ or a group —(O)(OPh)$_2$, n is an integer from 3 to 10000, and Ph is as defined above; and (3) crosslinked phenoxyphosphazene compound prepared by crosslinking at lease one phosphazene compound selected from the above cyclic phenoxyphosphazene compound and chain-like phenoxyphosphazene compound with at least one crosslinking group selected from o-phenylene group, m-phenylene group, p-phenylene group and a bisphenylene group which is represented by formula

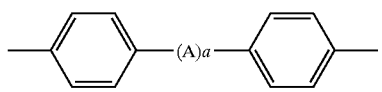

wherein A represents —C(CH$_3$)$_2$—, —SO$_2$—, —S— or —O— and a is 0 or 1, the crosslinked phenoxyphosphazene compound having the following characteristics:

(i) each of the crosslinking groups is interposed between two oxygen atoms left after the elimination of phenyl groups of the phosphazene compound;

(ii) the amount of the phenyl groups in the crosslinked compound is 50 to 99.9% based on the total amount of the phenyl groups in the phosphazene compound (1) and/or (2); and (iii) the crosslinked phenoxyphosphazene compound has no free hydroxyl groups in the molecule.

3. The method according to claim 1, wherein the phenoxyphosphazene compound is treated with the adsorbent.

4. The method according to claim 1, wherein the phenoxyphosphazene compound is treated with the reagent.

5. The method according to claim 4, wherein the reagent is at least one member selected from the group consisting of sodium borohydride, sodium thiosulfate, dimethyl sulfuric acid, triethyl ortho acetate, diazomethane and 1,3-propanesultone.

6. A method for producing a flame-retardant resin composition, comprising providing a phenoxyphosphazene compound having an acid value of lower than 0.025 mgKOH/g according to claim 1, and mixing the phenoxyphosphazene compound and a synthetic resin to produce the flame-retardant resin composition.

7. The method according to claim 6, wherein the synthetic resin is a polycarbonate resin or a mixed resin of polycarbonate resin and at least one of other resins.

8. The method according to claim 7, wherein said other resin is ABS resin.

* * * * *

UNITED STATES PATENT AND TRADEMARK OFFICE
CERTIFICATE OF CORRECTION

PATENT NO. : 6,946,578 B2
DATED : September 20, 2005
INVENTOR(S) : Shinji Nakano et al.

It is certified that error appears in the above-identified patent and that said Letters Patent is hereby corrected as shown below:

<u>Title page,</u>
Insert Item -- [30]     Foreign Application Priority Data
           May 1, 2000    (JP) …………………………..2000-132114 --.

Signed and Sealed this

Tenth Day of January, 2006

JON W. DUDAS
*Director of the United States Patent and Trademark Office*